United States Patent [19]
Thetford et al.

[11] Patent Number: 6,051,627
[45] Date of Patent: Apr. 18, 2000

[54] PHOSPHATE ESTERS OF POLYALKYLENE ETHER BLOCK COPOLYMERS AND THEIR USE AS DISPERSANTS

[75] Inventors: Dean Thetford, Rochdale; Mark Holbrook, Bury, both of United Kingdom

[73] Assignee: Zeneca Limited, London, United Kingdom

[21] Appl. No.: 09/077,866

[22] PCT Filed: Oct. 18, 1996

[86] PCT No.: PCT/GB96/02544

§ 371 Date: Jun. 1, 1998

§ 102(e) Date: Jun. 1, 1998

[87] PCT Pub. No.: WO97/19748

PCT Pub. Date: Jun. 5, 1997

[30] Foreign Application Priority Data

Nov. 30, 1995 [GB] United Kingdom ............... 9524476

[51] Int. Cl.$^7$ .................. C08G 65/04; C09D 171/02; C09D 11/02; C09U 11/16; C08L 71/02

[52] U.S. Cl. .................. 523/160; 523/161; 523/423; 528/419; 524/505; 525/409

[58] Field of Search ............... 523/160, 161, 523/423; 106/31.13, 31.6, 31.62, 31.85, 31.9; 525/409; 528/419

[56] References Cited

U.S. PATENT DOCUMENTS

| | | | |
|---|---|---|---|
| 2,674,619 | 4/1954 | Lunsted | 460/198 |
| 2,677,700 | 5/1954 | Jackson et al. | 568/618 |
| 3,029,216 | 4/1962 | Bailey, Jr. | 528/414 |
| 3,595,968 | 7/1971 | Groves et al. | 510/228 |
| 4,183,766 | 1/1980 | Woodward | 106/151.1 |
| 4,629,748 | 12/1986 | Miyajima et al. | 523/161 |
| 4,966,621 | 10/1990 | Heinrich et al. | 504/317 |
| 5,324,354 | 6/1994 | Jesse et al. | 106/413 |
| 5,412,021 | 5/1995 | Nakanishi | 524/523 |

FOREIGN PATENT DOCUMENTS 197 001 10/1986 European Pat. Off. .
395 988 11/1990 European Pat. Off. .

OTHER PUBLICATIONS

Lewis Sr., Richard J.; Hawley's Condensed Chemical Dictionary 12th Ed., John Wiley and Sons, New York (p. 435) 1993.

Chemical Abstracts, vol 117, No 24, Dec. 14, 1992, abstract No 237031, XP002023796, abstract; RN: 144636–11–3, 144636–12–4; 144636–13–5 & JP 04 100 894 A.

Chemical Abstracts, vol 117, No 6, Aug. 10, 1992, abstract No 50999, XP002023797, abstract; RN: 142297–64–1, & JP 04001 281 A.

Chemical Abstracts, vol 109, No 26, Dec. 26, 1988, abstract No 236726; XP002023798, abstract; RN: 71662–44–7 & JP 62 286 914 A.

Chemical Abstracts, vol 107, No 22, Nov. 30, 1987, abstract No 204923, XP002023799, abstract; RN: 68855–19–6, 68855–20–9 & JP 62 148 418 A.

*Primary Examiner*—Vasu Jagannathan
*Assistant Examiner*—Callie E. Shosho
*Attorney, Agent, or Firm*—Pillsbury Madison & Sutro LLP

[57] ABSTRACT

A dispersant which is a phosphate ester of a polyalkylene ether block copolymer of formula $MeO(C_2H_4O)_m(C_3H_6O)_n$—H wherein m and n are each, independently, 2 to 60 and use in aqueous based paints and printing inks.

11 Claims, No Drawings

PHOSPHATE ESTERS OF POLYALKYLENE ETHER BLOCK COPOLYMERS AND THEIR USE AS DISPERSANTS

This application is the national phase of international application PCT/GB96/02544 filed Oct. 18, 1996 which designated the U.S.

The present invention relates to a compound for dispersing particulate solids in an aqueous medium, its method of preparation and compositions containing said compound and a particulate solid, including paints and inks.

Mill-bases for water-borne paints are conventionally prepared by subjecting an aqueous medium containing a water-insoluble particulate solid such as a pigment to a grinding operation in the presence of both a resin and a dispersing agent in order to uniformly distribute the finely divided solid throughout the medium. However, when such mill-bases are added to a paint, the dispersing agent can adversely effect the film-forming characteristics of the paint and/or its durability as a paint film. Some dispersing agents also adversely affect the gloss of the resulting paint film. Consequently, improved dispersing agents are required which are capable of dispersing greater amounts of particulate solid in the medium, and exhibiting increased stability of the dispersion and superior properties in the resulting paint film, especially higher gloss finish.

According to the present invention there is provided a dispersant which is a phosphate ester of a poly($C_{2-3}$-alkylene glycol)-mono-$C_{1-4}$-alkyl ether of formula 1

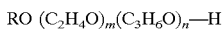  1 wherein

R is $C_{1-4}$-alkyl; and m and n are each, independently, 2 to 60.

R may be linear or branched but is preferably linear and is especially methyl.

Preferably, m is not less than 3 and especially not less than 5. It is also preferred that m is not greater than 45, more preferably not greater than 35 and especially not greater than 20.

Preferably, n is not less than 3, more preferably not less than 5 and especially not less than 7. It is also preferred that n is not greater than 40, more preferably not greater than 30 and especially not greater than 25.

The molecular weight of the mono alkyl ether of formula 1 is preferably less than 12,000, more preferably less than 8,000, even more preferably less than 5,000 and especially less than 3,000. It is also preferred that the molecular weight of the monoalkyl ether of formula 1 is not less than 400, more preferably not less than 800 and especially not less than 1,000.

The ratio of m to n is preferably between 1 to 3 and 3 to 1 and especially between 2 to 5 and 5 to 2.

The phosphate ester is obtainable by reacting the monoalkyl ether of formula 1 with a phosphating agent wherein the ratio of monoalkyl ether to each phosphorus atom of the phosphating agent is from 3:1 to 1:1 and especially from 2:1 to 1:1.

It is especially preferred that the ratio of monoalkyl ether to each phosphorus atom of the phosphating agent is less than 2, for example, about 1.5:1 when the dispersant is a mixture of mono- and di-phosphate esters.

The phosphate ester may be in the form of a free acid or it may form a salt with an alkali metal, ammonia, an amine, alkanolamine or a quaternary ammonium cation.

The phosphate ester may also be further reacted with an alkanol or alkanolamine. Preferred alkanols are $C_{1-6}$- and especially $C_{1-4}$-alkanols. When the phosphate ester is further reacted with the alkanol additional ester groups are formed and the ratio of the monoalkyl ether of formula 1 to the phosphorus atom of the phosphating agent is less than 2 and especially less than 1.5.

When the phosphate ester is reacted with an alkanolamine, the alkanolamine may form ester and/or amido groups and/or amine salts. It is believed that the reaction product is mainly an amine salt.

Preferred phosphating agents are $POCl_3$, polyphosphoric acid and especially $P_2O_5$.

Preferably, the alkali metal is lithium, potassium and especially sodium.

Examples of alkanolamines are ethanolamine, diethanolamine, 2-dimethylamino ethanol and 2-amino-2-methyl-1-propanol.

The monoalkyl ether of formula 1 is made by any method known to the art and is preferably made by reacting a polyethyleneglycol monoalkyl ether of formula 2 with propylene oxide

  2 wherein

R and m are as defined hereinbefore.

Typically, the monoalkyl ether of formula 2 is reacted with propylene oxide in an inert atmosphere such as nitrogen and under anhydrous conditions in the presence of an alkali metal. The alkali metal is preferably lithium, sodium and especially potassium. The alkali metal is conveniently added to the monoalkyl ether of formula 2 as a water soluble inorganic salt, especially a hydroxide and the water removed by heating, especially heating under reduced pressure prior to adding the propylene oxide. Owing to the volatility of propylene oxide, its reaction with the monoalkyl ether of formula 2 is carried out in a closed vessel, generally at temperatures between 40 and 140° C. Preferably, the temperature is above 80 and especially above 100° C.

The reaction between the monoalkyl ether of formula 1 and the phosphating agent is also preferably carried out in an inert atmosphere such as nitrogen under anhydrous conditions. The reaction may be carried out in an inert solvent but is more convenient to react the monoalkyl ether with the phosphating agent in the absence of a solvent. The reaction temperature is preferably above 60 and especially above 80° C. In order to avoid charring of the dispersant, the temperature is preferably less than 120 and especially less than 100° C.

When the dispersant contains additional ester, amide and/or amine salt groups formed by reacting the phosphate ester with an alkanol or alkanolamine the alkanol or alkanolamine may be reacted with the phosphate ester under the same conditions as are used for reacting the monoalkyl ether with the phosphating agent.

As noted hereinbefore the dispersants according to the present invention are suitable for uniformly distributing a particulate solid in a liquid medium, especially an aqueous medium.

Thus, according to a further aspect of the invention there is provided a composition comprising a dispersant as defined hereinbefore and a particulate solid.

Preferably, the composition further comprises a liquid, especially one in which the dispersant is at least partially soluble and more especially is either water or an organic liquid which is miscible with water including mixtures thereof. Examples of suitable liquids include alcohols such as $C_{1-10}$-aliphatic alcohols; glycols such as $C_{2-6}$-alkylene glycols; alcohol ethers such as methoxy-, ethoxy-, propoxyand butoxyethanol and methoxy-, ethoxy- and propoxypropanol; and glycol ethers such as diethylene glycol and propylene glycol. Generally, the liquid is selected to meet the requirements of the end-use to which the composition is put, especially compatibility with any medium with which it is to be diluted. Preferably, the liquid comprises at least 25%, more preferably at least 50% and especially at least 75% by weight water relative to the total weight of the composition.

The composition may comprise an intimate mixture of the dispersant and the particulate solid but preferably comprises a coating of the dispersant on a finely divided particulate solid. Preferably the particulate solid has a mean diameter of less than 15$\mu$, more preferably less than 10$\mu$, especially less than 5$\mu$ and most especially less than 3$\mu$.

The particulate solid can be any material which it is desired to stabilise in a finely divided state in a liquid medium. Examples of suitable solids are pigments and fillers for inks, paints and other surface coatings; magnetic metals or alloys and magnetic oxides, for use in the production of magnetic tapes, discs and memory devices; dirt and soil particles; biocides, agrochemicals and pharmaceuticals. The composition, whether dry or in the form of a dispersion in a liquid medium, may contain other ingredients such as resins, binders, fluidising agents, anti-sedimentation agents, plasticisers, humectants, coalescents, co-solvents, thickeners and preservatives. These ingredients may be soluble in, partially soluble in, insoluble in, or dispersed in the liquid medium.

If the solid is a pigment, it is preferably an inorganic pigment, a metallic pigment, or a metal salt of an organic dyestuff (sometimes referred to as a lake or toner). It may come from any of the recognised classes of pigments described, for example in the Third Edition of the Colours Index (1971) and subsequent revisions and supplements thereto, under the chapter headed "Pigments".

Examples of inorganic pigments are titanium dioxide (including Anatase and Rutile forms, and high UV absorbing ultra-fine titanium dioxide), zinc oxide, Prussian Blue, cadmium sulphide, iron oxides (including transparent iron oxides), ultramarine, mica (including pearlescent pigments made by surface treating mica with, for example, fine titanium dioxide) and the chrome pigments, including chromates, molybdates, and mixed chromates and sulphates of lead, zinc, barium, calcium and mixtures and modifications thereof which are commercially available as greenish-yellow to red pigments under the names of primrose, lemon, middle, orange, scarlet and red chromes.

Examples of metallic pigments are aluminium flake, copper powder and copper flake.

Examples of metal salts of organic dyestuffs are the azo metal salt pigments such as Cl Pigment red 48 (also known as 2B Toner or Permanent Red 2B), Cl Pigment Red 53 (also known as Lake Red C or Red Lake C), Cl Pigment Red 52, Cl Pigment Red 57 (also known as 4B Toner, Lithol Rubine, Rubine Toner or Permanent Red 4B), Cl Pigment Red 58, Cl Pigment Red 247, Cl Pigment Yellow 61, Cl Pigment Yellow 62, Cl Pigment Yellow 183 and Cl Pigment Yellow 191.

Examples of fillers are calcium carbonate, hydrated alumina, talc, quartz, silica (precipitated, pyrogenic and synthetic), metal silicates, barium and calcium sulphate, china clay, antimony oxide, powdered slate, wollastonite and chopped glass fibre.

The composition may be made by any method known to the art. Thus, it may be prepared by mixing together the dispersant and particulate solid and preferably then grinding the composition to obtain the desired particle size of the solid. Preferably, however, the dispersant may be added to the particulate solid in the presence of a liquid during the final preparation or finishing stages of the particulate solid. Generally, the composition is, however, prepared by mixing the dispersant, particulate solid and a liquid medium and then grinding or milling the composition to obtain the desired particle size of the particulate solid. The liquid medium may be water or an organic liquid in which the dispersant is preferably at least partially soluble. If the composition is required in dry form, the liquid medium is preferably volatile so that it may be readily removed from the particulate solid by simple separation means such as evaporation. It is preferred however that the composition comprises the liquid medium.

If the dry composition consists essentially of the dispersant and the particulate solid, it preferably contains at least 0.2%, more preferably at least 0.5% and especially at least 1% by weight of dispersant based on the weight of the particulate solid. Preferably, the dry composition contains not greater than 100%, preferably not greater than 50%, more preferably not greater than 20% and especially not greater than 10% by weight dispersant based on the weight of the particulate solid.

When the composition comprises a dispersant, particulate solid and a liquid medium, it preferably contains at least 5%, more preferably at least 20%, especially at least 40% and most especially at least 50% particulate solid based on the total weight of the composition. Preferably, the composition contains not greater than 90%, more preferably not greater than 80% and especially not greater than 75% by weight solid based on the total weight of the composition. The preferred amount of dispersant relative to the particulate solid is as defined hereinbefore for the dry composition.

As described hereinbefore, the dispersants of the invention are particularly suitable for preparing aqueous mill-bases where the particulate solid is milled in a liquid in the presence of both the dispersant and a film-forming resin binder.

Thus, according to a still further aspect of the invention there is provided an aqueous mill-base comprising a particulate solid, dispersant and a film forming resin.

Typically, the mill-base contains from 20 to 70% by weight particulate solid based on the total weight of mill-base. Preferably, the particulate solid is not less than 30 and especially not less than 50% by weight of the mill-base.

The amount of resin in the mill-base can vary over wide limits but is preferably not less than 10%, and especially not less than 20% by weight of the continuous phase/liquid phase of the mill-base. Preferably, the amount of resin is not greater than 50% and especially not greater than 40% by weight of the continuous phase/liquid phase of the mill-base.

The amount of dispersant in the mill-base is dependent on the amount of the particulate solid but is preferably from 0.5 to 5% by weight of the mill-base.

The resin may be any film-forming resin which is capable of acting as a binder in aqueous paints and printing inks. The resin is preferably capable of undergoing a cross-linking action with a cross-linker and is preferably an acrylic or acrylate copolymer containing ethylenically unsaturated groups.

The invention is further illustrated by the following examples in which all parts and percentages refer to amounts by weight unless indicated to the contrary.

Intermediate Polyalkyleneglycol Monoalkyl Ethers

In the following preparative details of block co-polymers, the polyethylene glycol monomethyl ether is referred to as MeO PEG and polypropylene glycol as PPG. The approximate molecular weight of the polymer chains are given in parentheses.

Intermediate 1

MeO PEG (750) PPG (650)

MeO PEG (750) (750 parts;1M ex Fluka) was charged to a reaction vessel together with a solution of potassium hydroxide (14.1 parts) in distilled water (14.1 parts). The vessel was heated with stirring to 110° C. at 20 to 30 mm Hg to remove the water. Propylene oxide (750 parts; 12.9M) was then added and the vessel heated with stirring at 110° C. for 8 hours until the reaction was complete. Any unreacted propylene oxide was removed at 110° C. and 20 to 30 mm Hg. The block co-polymer (1514 parts) was obtained as a red brown oil which solidified on cooling. It contains PEG:PPG ratio of about 1.5:1.

Intermediate 2

MeO PEG (750) PPG (1260)

This was prepared by the method described for Intermediate 1 except that the amount of propylene oxide was increased to 1400 parts. The block co-polymer (1863 parts) was obtained as a light brown oil and contains a PEG:PPG ratio of about 1:1.4.

Intermediate 3

MeO PEG (350) PPG (930)

This was prepared by a similar process to that for Intermediate 1 except using MeO PEG (350) (350 parts; 1M; ex Fluka). The block co-polymer was obtained as a dark brown oil. The co-polymer contains a PEG:PPG ratio of about 2:1 and had an OH value of 48 mgs KOH/gm (Effective MW=1190).

Intermediate 4

MeO PEG (550) PPG (700)

This was prepared by the method described for Intermediate 1 except using MeO PEG (550) (550 parts; M; ex Fluka) and propylene glycol (700 parts; 12M). The block co-polymer was obtained as a dark yellow oil with a PEG:PPG ratio of about 1:1. The OH value was found to be 50.6 mgs KOH gm$^{-1}$ with an effective MW of 1109.

Intermediate 5

MeO PEG (750) PPG (500)

This was prepared by the method described for Intermediate 2 except using MeO PEG (750) (750 parts; 1M). The block co-polymer was obtained as a dark brown oil; with a PEG:PPG ratio of about 2:1. The OH value was found to be 50.8 mgs KOH gm$^{-1}$ with an effective MW of 1104.

PREPARATION OF DISPERSANTS

EXAMPLE 1

MeO PEG (750) PPG (650) (1:1 phosphorus)

Intermediate 1 (28 parts; 0.02M) was charged to a reaction vessel sparged with nitrogen. Phosphorus pentoxide (1.42 parts; 0.01M) was added at 20–25° C. and the reactants stirred rapidly for 15 minutes. The temperature was then raised to 80° C. After stirring at 80° C. for 2 hours a white solid gradually formed which on stirring at 80° C. under nitrogen, for a further 16 hours dissolved forming a pale yellow oil containing a little solid. The temperature was raised to 90° C. and the reactants stirred for a further 16 hour under nitrogen when the solid dissolved. This is Dispersant 1 and was obtained as a clear yellow oil which solidified on cooling.

EXAMPLE 2

MeO PEG (750) PPG (1260) (1:1 phosphorus)

This was prepared by a similar method to that described in Example 1 except using Intermediate 2 (30 parts; 0.015M) in place of Intermediate 1 and phosphosphorus pentoxide (1.06 parts; 0.0075 M). However, in this preparation the reactants were stirred for a total of 21 hours at 80° C. after addition of the pentoxide. This is Dispersant 2 and was obtained a pale brown oil.

EXAMPLE 3

MeO PEG (350) PPG (930) (1.5:1 phosphorus)

Intermediate 3 (35.67 parts, 0.03M) was charged to a reaction vessel and sparged with nitrogen. Phosphorus pentoxide (1.42 parts; 0.01M) was added and the reactants stirred at 20–25° C. for 1 hour under a nitrogen blanket. The pentoxide dispersed rapidly and the reactants were stirred at 80–90° C. under nitrogen for a further 16 hours. This is Dispersant 3 and was obtained as a clear yellow oil.

EXAMPLE 4

MeO PEG (550) PPG (700) (1.5:1 phosphorus)

This was prepared by the method described in Example 3 except replacing Intermediate 3 with Intermediate 4 (33.27 parts; 0.03 M). This is Dispersant 4 and was obtained as a clear yellow oil.

EXAMPLE 5

MeO PEG (750) PPG (500) (1.5:1 phosphorus)

This was prepared by the method described in Example 3 except replacing Intermediate 3 with Intermediate 5 (33.12 parts; 0.03 M). This is Dispersant 5 and was obtained as a light brown oil which formed a soft paste on standing.

EXAMPLE 6

MeO PEG (750) PPG (650) (1.5:1 phosphorus)

Intermediate 1 (100 parts) was stirred with polyphosphoric acid (7.94 parts; containing 85% $P_2O_5$) at 90° C. for 24 hours in a nitrogen atmosphere giving a brown oil (104 parts) which on cooling gave a waxy solid. This is Dispersant 6.

EXAMPLE 7

MeO PEG (750) PPG (1260) (1.5:1 phosphorus)

Intermediate 2 (100 parts) was stirred with polyphosphoric acid (5.54 parts) at 90° C. for 24 hours under nitrogen to give a brown oil (103 parts) which on cooling gave a waxy solid. This is Dispersant 7.

EXAMPLE 8

MeO PEG (350) PPG (930) (1:1 phosphorus)

This was prepared in similar manner to Dispersant 6 except using Intermediate 3 (100 parts) in place of Intermediate 1 and reacting with 13.05 parts polyphosphoric acid. On cooling Dispersant 8 was obtained as a dark brown viscous oil (110 parts).

EXAMPLE 9

MeO PEG (550) PPG (700) (1:1 phosphorus)

This was prepared in similar manner to Dispersant 6 except using Intermediate 4 (100 parts) in place of Intermediate 1 and reacting with 13.39 parts polyphosphoric acid. Dispersant 9 was obtained as a dark brown viscous oil (108 parts).

EXAMPLE 10

MeO PEG (750) PPG (500) (1:1 phosphorus)

This was again prepared in similar manner to Dispersant 6 except using Intermediate 5 (100 parts) in place of Intermediate 1 and reacting with 13.42 parts pyrophosphoric acid. Dispersant 10 was obtained as a dark brown viscous liquid (109 parts).

EXAMPLES 11 TO 13

Evaluation of Dispersants in Millbases

Millbases were prepared by ball milling the ingredients listed in Table 1 below in a high energy ball mill with 3 mm glass beads (125 parts) for 30 minutes.

After milling, the resultant millbase was converted into a usable paint by dilution with a letdown emulsion in Table 1.

Test panels were prepared by coating aluminium and primed steel panels using a mechanised wire wound K bar draw down system supplied by RK Print-Coat Instruments Ltd, Royston, Herts, England. The K bar was calibrated to leave a wet film thickness of 100 microns. The paint films were allowed to dry at ambient temperature for 30 minutes and then baked at 120° C. for 30 minutes. The average 20° gloss of each panel was calculated from the mean of 5 readings taken over the panel surface. The results are given in Table 2.

TABLE 1

| Millbase | Example 11 | Example 12 | Example 13 |
| --- | --- | --- | --- |
| Dispersant 3 | 1.02 | | |
| Dispersant 4 | | 1.02 | |
| Dispersant 5 | | | 1.02 |
| Water | 3.74 | 3.74 | 3.74 |
| Neocryl XK90 | 17.92 | 17.92 | 17.92 |
| Dehydran 1293 | 0.23 | 0.23 | 0.23 |
| Tioxide TR 92 | 25.6 | 25.6 | 25.6 |
| Propylene glycol | 2.7 | 2.7 | 2.7 |
| Letdown | | | |
| Yield of paint | 30.75 | 30.75 | 30.75 |
| Neocryl XK90 | 53.2 | 53.2 | 53.2 |

Footnote to Table 1
Aqueous solutions of Dispersants 6–8 are acidic and so the pH was raised to pH 9 ± 1 by addition of ammonia prior to addition of the Neocryl resin. The paints were let down to final volume by adding Neocryl XK90 resin in the amounts given by the formula Weight of Neocryl resin = $Y \times \dfrac{212.4}{122.8}$ where Y is the yield of millbase.

TABLE 2

| | Average 20° gloss | |
| --- | --- | --- |
| Example | Aluminium panel | Primed steel |
| 11 | 60.7 | 60.78 |
| 12 | 60.86 | 60.40 |
| 13 | 58.18 | 60.10 |

EXAMPLES 14, 15 and COMPARATIVE EXAMPLES A To C

Millbases were prepared using Dispersants 1 and 2 in Examples 14 and 15 using the method described in Example 11 to 13. Both Dispersants 1 and 2 contain a block co-polymer to phosphorus ratio of 1:1. These are compared with dispersants A, B and C which also contain a block co-polymer to phosphorus ratio of 1:1 but where the co-polymer is a MeO PEG block co-polymer i.e. the PPG and PEG segments are reversed compared with Dispersants 1 and 2.

The 20° gloss measurements of these millbases are given in Table 3 below and show that those dispersants derived from block co-polymers of general formula MeO(PEG)(PPG) are superior to those derived from block co-polymers of general formula MeO(PPG)(PEG), especially where the millbase is applied to primed steel panels.

TABLE 3

| | | Average 20° gloss | |
| --- | --- | --- | --- |
| Example or Comp. Example | Dispersing Agent | Aluminium panel | Primed Steel |
| 14 | 1 | 39.3 | 36.0 |
| 15 | 2 | 40.9 | 36.5 |
| A | A | 34.96 | 34.32 |
| B | B | 33.24 | 32.46 |
| C | C | 40.02 | 34.04 |

Footnote to Table 3
Dispersing Agents A–C contain an alkoxyalkanol to phosphorus ratio of 1:1.
A is derived from MeO PPG (650) PEG (900)
B is derived from MeO PPG (900) PEG (660)
C is derived from MeO PPG (1200) PEG (450)

EXAMPLEs 16 TO 25

Millbases were prepared by dissolving the dispersant (2.55 parts) and Dehydran 1295 (0.3 parts) in a mixture of water (9.6 parts) propylene glycol (6.75 parts) and 2-amino-2-methyl-1-propanol (0.23 parts) with warming having first adjusted the pH to about 10. The resulting solution was cooled and poured into a dispermat pot. Neocryl XK90 (44.8 parts) and Tioxide TR92 (64 parts) were added together with 1 mm glass beads (180 parts) and the millbase milled at speed setting 3000 for 30 minutes with no external cooling. The resulting millbase was then separated from the glass beads and let down with further Neocryl XK90 in the amount shown in Table 4 below. Dehydran 1293 is an antifoam available from Henkel GmbH, Neocryl XK90 is an acrylic resin in water/propylene glycol available from Zeneca Resins and Tioxide TR92 is titanium dioxide available from ICI PLC.

TABLE 4

| Example | Dispersant | Yield of paint | Amount of Neocryl XK90 letdown |
|---|---|---|---|
| 16 | 1 | 26.05 | 27.02 |
| 17 | 2 | 50.62 | 52.50 |
| 18 | 3 | 39.3 | 40.76 |
| 19 | 4 | 25.8 | 26.76 |
| 20 | 5 | 8.53 | 8.85 |
| 21 | 6 | 51.77 | 53.70 |
| 22 | 7 | 63.33 | 65.69 |
| 23 | 8 | 63.72 | 66.09 |
| 24 | 9 | 66.78 | 69.26 |
| 25 | 10 | 64.23 | 66.62 |

Footnote to Table 4
The amount of Neocryl XK90 (X) used as letdown was calculated from the formula $$X = \frac{Y \times 133}{128.23}$$

where Y is the yield of paint.

When Dispersants 1–10 were replaced by MeO PEG (750) phosphated (1.5:1 phosphorus) it failed to produce a dispersion. This shows the advantage of the PPG polymer chain adjacent to the phosphate moiety.

The above paints were allowed to stand overnight (16 hours) to de-aerate and were then coated onto primed steel and aluminium panels as described in Examples 11 to 13. The 20° average gloss of the paints are detailed in Table 5 below.

TABLE 5

| Example | Dispersant | Average 20° gloss | |
|---|---|---|---|
| | | Aluminium | Primed Steel |
| 16 | 1 | 60.2 | 52.53 |
| 17 | 2 | 58.32 | 49.96 |
| 18 | 3 | 57.42 | 51.66 |
| 19 | 4 | 59.92 | 51.96 |
| 20 | 5 | 55.74 | 48.10 |
| 21 | 6 | 60.88 | 52.06 |
| 22 | 7 | 55.56 | 50.16 |
| 23 | 8 | 59.00 | 53.28 |

TABLE 5-continued

| Example | Dispersant | Average 20° gloss | |
|---|---|---|---|
| | | Aluminium | Primed Steel |
| 24 | 9 | 60.58 | 56.64 |
| 25 | 10 | 55.82 | 52.82 |

We claim:

1. A dispersant which is a phosphate ester of a polyalkylene ether block copolymer of formula 1

$$RO(C_2H_4O)_m(C_3H_6O)_n\text{—}H \quad\quad 1$$

wherein

R is $C_{1-4}$-alkyl; and m and n are each, independently, 2 to 60.

2. A dispersant as claimed in claim 1 wherein R is methyl.

3. A dispersant as claimed in either claim 1 or claim 2 wherein the ratio of m to n is between 2:5 and 5:2.

4. An aqueous millbase comprising a dispersant as claimed in claim 3, a particulate solid and a film-forming resin.

5. A paint or ink comprising a dispersant as claimed in claim 3, a particulate solid and a film-forming resin.

6. A dispersant as claimed in claim 1 which is a mixture of mono- and di-phosphate.

7. An aqueous millbase comprising a dispersant as claimed in any one of claims 1, 2, or 6, a particulate solid and a film-forming resin.

8. A paint or ink comprising a dispersant as claimed in any one of claims 1, 2, or 6, a particulate solid and a film-forming resin.

9. A composition comprising a dispersant as claimed in claim 1 and a particulate solid.

10. A composition as claimed in claim 9 which additionally comprises liquid medium.

11. A composition as claimed in claim 10 wherein the liquid medium is water.

* * * * *